United States Patent [19]
Taheri

[11] Patent Number: 6,017,718
[45] Date of Patent: Jan. 25, 2000

[54] URINE SOLUBLE TUMOR NECROSIS FACTOR RECEPTOR FOR DIAGNOSIS OF DEEP VENOUS THROMBOSIS

[76] Inventor: Syde A. Taheri, 1275 Delaware Ave., Buffalo, N.Y. 14209

[21] Appl. No.: 09/135,761

[22] Filed: Aug. 18, 1998

[51] Int. Cl.⁷ .......................... G01N 33/53; C12P 21/06; C12P 21/021; A61K 39/395
[52] U.S. Cl. .......................... 435/7.1; 435/7.1; 435/69.1; 435/69.7; 435/69.6; 424/133.1; 424/145.1
[58] Field of Search ...................... 435/7.1, 69.6, 435/69.7, 69.1; 424/133.1, 145.1

[56] References Cited

PUBLICATIONS

S. Taheri et al., (Angiology—The Journal of Vascular Diseases, vol. 49, No. 7, 1998) Diagnosis of Deep Venous Thrombosis by Use of Soluble Necrosis Factor Receptor.

Seckinger et al, A human inhibitor of tumor necrosis factor alpha, J.Exp.Med, vol., 157, pp. 1511–1516, 1988.

Zangerle et al, Tumor necrosis factor alpha and soluble tumor necrosis factor receptors in individuals with human immunodeficiency virus infection, Immunology letters, vol., 41, pp. 229–234, 1994.

*Primary Examiner*—Nita Minnifield
*Assistant Examiner*—Padma Baskar
*Attorney, Agent, or Firm*—Hodgson, Russ, Andrews, Woods & Goodyear LLP

[57] ABSTRACT

A method for predicting the presence of deep venous thrombosis in a patient comprises measuring the concentration of soluble tumor necrosis factor receptor-1 (p55) in the patient's urine and comparing the measured concentration to an established baseline concentration. A concentration in the patient's urine greater than the established baseline concentration is predictive of the presence of deep venous thrombosis.

4 Claims, No Drawings

URINE SOLUBLE TUMOR NECROSIS FACTOR RECEPTOR FOR DIAGNOSIS OF DEEP VENOUS THROMBOSIS

BACKGROUND OF THE INVENTION

FIELD OF THE INVENTION

This invention relates to a screening method useful for the detection of deep vein thrombosis.

Deep venous thrombosis (DVT) is a relatively common and extremely serious disorder that may be potentially fatal since it may lead to pulmonary emboli (PE). DVT is common in patients who are immobilized for relatively long periods of time as a result of a medical or surgical illness, or patients with multiple trauma or malignant diseases. It also occurs commonly in persons who are immobilized or of limited mobility as a result of being paraplegic or quadriplegic and may also develop in otherwise healthy persons after prolonged sitting or immobilization.

Clinical diagnosis of deep venous thrombosis and pulmonary emboli is correct only about 50% of the time. Furthermore, diagnostic tests, such as ultrasound, venous imaging, radioactive fibrinogen, venous plethysmography, venography, and magnetic resonance venography may not be cost-effective screening tools. These tests may also be invasive, or the results may be subject to operator-dependent interpretation.

SUMMARY OF THE INVENTION

With recent advances in molecular biology, and better understanding of the interaction between the endothelial cell and the inflammatory cell, a new blood test for soluble tumor necrosis factor (TNF) receptors has proven to be a diagnostic test for DVT and consequently PE. The pathogenesis of DVT has been attributed to stasis hypercoagulability and inflammation. However, recent information shows the interaction of inflammatory procoagulant cytokines, inflammatory cells, and venous endothelium to be the first step in activating the clotting cascade. Cytokines such as TNF and P-selectin up-regulate tissue factor expression and down-regulate protein C and thrombomodulin. This ultimately leads to clot formation.

It has now been determined that the presence of deep venous thrombosis in a patient is detectable in a relatively simple and effective manner by measuring the concentration of soluble tumor necrosis factor receptor-1 (p55) present in a sample of the patient's urine and comparing that concentration to an established baseline concentration of soluble tumor necrosis factor receptor-1. According to the present invention, the presence of, or development of, deep venous thrombosis is then predictable if the concentration of soluble tumor necrosis factor receptor-1 in the urine sample exceeds that of the established baseline.

Although not intending to be bound by any particular theory, it is postulated that the production of cytokines, in particular the cytokine known as tumor necrosis factor-alpha (TNF-α) (also known as cachetin), a cytotoxic protein produced by lymphocytes in the human body, plays an important role in the genesis of deep vein thrombosis and the evolution of this disease. Consequently, soluble tumor necrosis factor receptor-1 is generated by inflammatory cells during clot formation and is a surrogate marker for inflammatory diseases in which tumor necrosis factor plays an important role. According to the present invention and based on studies detailed hereinbelow, in patients with deep venous thrombosis, the concentration of soluble tumor necrosis factor receptors, particularly soluble tumor necrosis factor receptor-1, is markedly increased and reflects the activity of inflammatory cells in deep venous thrombosis.

DETAILED DESCRIPTION OF THE INVENTION

Tumor necrosis factors are polypeptide cytokines that are produced by mononuclear cells; their function may cause a severe inflammatory response. TNF receptors have a high affinity to TNF and play a key role in the initiation and control of the cellular response to those cytokines.

Soluble forms of TNF receptors bind to TNF and can interfere with its binding to the membrane-bound receptors. It is suggested, therefore, that soluble tumor necrosis factors function as physiological inhibitors of TNF activity at the cellular membrane.

In venous thrombosis, the venous wall is infiltrated by activated neutrophils, macrophages, and other inflammatory cells, which contribute to the disease process and eventual clot formation. Because cytokines and the adhesive molecules produced by these activated cells are the major modulators of inflammatory functions, much attention has been focused on the role of these molecules. The detection of cytokines and inflammatory cells in the venous wall has prompted efforts to determine whether local production of these cytokines may play an important role in the genesis and evolution of DVT. These cytokines can often induce themselves, activate a cascade of other cytokines, or synergize or antagonize each other's effects.

TNF is a potent polypeptide that induces many other cytokines, including the soluble tumor necrosis factor receptor-1 (p55). TNF-α mediates the effects of TNF by binding to either of the soluble tumor necrosis factor receptors p55 or p75 to transmit signals to the cytoplasm. It has been reported that both of these TNF receptors are abundant in cells that produce TNF-α, suggesting that autocrine or paracrine stimulation is a constant ongoing process. Despite the coexistence of TNF and TNF receptors, insufficient amounts of receptors are present to prevent the deleterious effect of overproduced TNF. This discrepancy must be attributed to the presence of soluble TNF receptors, which are now known to act as native inhibitors. A number of soluble cytokine receptors are also present in plasma. The soluble TNF receptors are generated through elastase proteolytic cleavage of the p75 receptors.

Since soluble TNF receptors are shed forms of the transmembrane TNF-α receptor, it is believed that soluble TNF receptors may act as a regulator of TNF-α activity at the cellular membrane.

Accordingly, the rapid clearance of TNF from the circulation and the binding of TNF-α to receptors provides soluble TNF receptor determination as an alternative marker for diagnosis of DVT. Additionally, the long half-life of soluble TNF receptors means that, according to the present invention, these cytokines are useful as a marker for the diagnosis and evolution of DVT. Furthermore, it would seem that the degree of elevation of TNF levels may correlate with the amount of clot present. Hence, determination of TNF levels in the urine is useful as a quick, non-invasive test for the diagnosis of DVT. The data suggests that three categories are detectable: (1) a normal level where DVT is ruled out, (2) an intermediate level where the diagnosis of DVT should be further evaluated, and (3) a high level diagnostic for DVT.

The concentration of soluble tumor necrosis factor receptor-1 (p55) in a sample of urine is determined by the assay procedure known as ELISA. The procedure is as follows:

(1) A monoclonal antibody specific for the soluble tumor necrosis factor receptor-1 is pre-coated onto a microtiter plate.

(2) Standards and samples are pipetted into the wells and any soluble tumor necrosis factor receptor-1 present is bound by the immobilized antibody.

(3) After washing away any unbound substances, an enzyme-linked polyclonal antibody specific for soluble tumor necrosis factor receptor-1 is added to the wells.

(4) After a wash to remove any unbound antibody-enzyme reagent, a substrate solution is added to the wells and color develops in proportion to the amount of soluble tumor necrosis factor receptor-1 bound in the initial step.

(5) The color development is stopped and the intensity of the color is measured and compared to a standard.

Study Procedure

Forty patients with DVT (16 men, 24 women), including six patients with PE, were studied. Their ages ranged from 34 to 74 years old with a mean age of 45 years. Sixteen healthy volunteers, eight men and eight women, ranging in age from 30 to 70 years old, served as control subjects.

Work-up included complete blood count, blood chemistry, sedimentation rate, and rheumatoid factors. Ultrasound imaging and ventilation perfusion (V/Q) scans were used for diagnosis of DVT and PE.

Five-milliliter blood sample were obtained from each subject via venipuncture and placed in citrated test tubes. These samples were subjected to a solid-phase enzyme-linked immunosorbent assay (ELISA) analysis for TNF-α.

In brief, 50 µl of assay dilutent was added to the wells of an antibody-coated microtiter plate. Then, 200 Al of patient plasma prepared from whole blood was added. After a 2-hour incubation, each well was washed three times. Then, 200 µl of the receptor conjugate was added and incubated for 2 hours, after which the plate was washed three times and 200 µl of substrate was added. A 40 ml stop solution was added to each well and the microtiter plate reader spectrophotometer was set to 450 nm.

Symptoms among the patients included the following: leg pain (19), chest pain (six), lower extremity edema (25), shortness of breath (six), and varicose veins (four). Deep venous thrombosis was present in the locations shown in Table 1.

TABLE 1

Location of DVT

| Location | No. of DVTs |
|---|---|
| Right femoral vein | 8 |
| Left femoral vein | 10 |
| Left iliofemoral vein | 2 |
| Right axillary vein | 1 |
| Pulmonary emboli | 5 |
| Calf vein | 6 |
| Bilateral femoral vein | 8 |

The average normal soluble TNF receptor in the urine of control subjects was about zero. In patients with DVT and PE, the average was 1,720 pg/ml with a range of about 650 to about 5,000 pg/ml. The amount of soluble TNF receptor was greatest in bilateral cases and pulmonary emboli compared with unilateral cases or calf vein thrombosis.

Based on the findings, it is considered that a baseline concentration of soluble tumor necrosis factor receptor-1 (p55) of about 10 to about 500 pg/ml may be used for purposes of prediction of deep vein thrombosis. Accordingly, if the concentration of soluble tumor necrosis factor receptor-1 (p55) in a sample of urine is higher than that, the presence of deep vein thrombosis may be predicted in the patient.

It is appreciated that various modifications to the present inventive concepts described herein may be apparent to those of ordinary skill in the art without disparting from the spirit and scope of the present invention as defined by the herein appended claims.

What is claimed is:

1. A method for predicting the presence of deep venous thrombosis in a patient, comprising the steps of:

a) obtaining a sample of urine from the patient;

b) measuring the concentration of soluble tumor necrosis factor receptor-1 in the sample;

c) comparing the concentration of soluble tumor necrosis factor receptor-1 in the sample to an established baseline concentration of soluble tumor necrosis factor receptor-1, wherein said established baseline concentration of soluble tumor necrosis factor receptor-1 is at least 10 picograms/milliliter to about 500 picograms/milliliter of urine and wherein a measured concentration of soluble tumor necrosis factor greater than the established baseline concentration is predictive of the presence of deep venous thrombosis in the patient; and d) predicting the presence of, or development of, deep venous thrombosis in the patient if the concentration of soluble tumor necrosis factor receptor-1 in the sample is greater than the established baseline concentration of soluble tumor necrosis factor receptor-1.

2. The method of claim 1 wherein the concentration of soluble tumor necrosis factor receptor-1 is determined by an assay procedure.

3. The method of claim 2 wherein the assay procedure is ELISA.

4. The method of claim 1 wherein a soluble tumor necrosis factor receptor-1 concentration of about 500 picograms/milliliter to about 5,000 picograms/milliliter of the urine sample is diagnostic of the presence of deep venous thrombosis in the patient.

* * * * *